US00PP18934P2

(12) United States Plant Patent
Hardison et al.

(10) Patent No.: US PP18,934 P2
(45) Date of Patent: Jun. 17, 2008

(54) HYBRID VARIETY OF BLUEGRASS DESIGNATED 'HB 328'

(50) Latin Name: ***Poa arachnifera Torr.×Poa pratensis* L.**
Varietal Denomination: HB 328

(75) Inventors: John R. Hardison, Corvallis, OR (US); Jay B. Burr, Salem, OR (US); James R. Frelich, Salem, OR (US); George Marquez, Albany, OR (US)

(73) Assignee: OMS Investments, Inc., Los Angeles, CA (US)

( * ) Notice: Subject to any disclaimer, the term of this patent is extended or adjusted under 35 U.S.C. 154(b) by 24 days.

(21) Appl. No.: 11/506,027

(22) Filed: Aug. 17, 2006

(51) Int. Cl.
*A01H 5/00* (2006.01)

(52) U.S. Cl. ..... Plt./393
(58) Field of Classification Search ..... Plt./393, Plt./388
See application file for complete search history.

(56) References Cited

U.S. PATENT DOCUMENTS

PP9,977 P 7/1997 Meier et al. ..... Plt./90.2

OTHER PUBLICATIONS

U.S. Appl. No. 11/197,945, filed Aug. 5, 2005.
U.S. Appl. No. 60/599,539, filed Aug. 6, 2004.
U.S. Appl. No. 11/208,473, filed Aug. 19, 2005.
U.S. Appl. No. 11/483,919, filed Jul. 10, 2006.

*Primary Examiner*—Anne Marie Grunberg
*Assistant Examiner*—June Hwu
*Assistant Examiner*—
(74) *Attorney, Agent, or Firm*—James B. Raden; Welsh & Katz Ltd

(57) ABSTRACT

A hybrid variety of (Texas bluegrass×Kentucky bluegrass)× Kentucky bluegrass is described, characterized by a moderately rapid establishment; dark green color; short plant height; semi-erect growth habit; short tiller culms; a moderately wide leaf blade; large seed; short flag leaf; moderately aggressive rhizome growth; high cold resistance; and high resistance to rust and dollarspot diseases.

3 Drawing Sheets

BACKGROUND OF THE INVENTION

Field of the Invention

The present invention relates to a new and distinct hybrid variety *Poa arachnifera* Torr.×*Poa pratensis* L. that has been designated as 'HB 328' bluegrass.

Description of Related Art

A Texas Bluegrass×Kentucky Bluegrass hybrid designated 'Reveille' has been disclosed in PVP Certificate No. 9800337. Another *Poa arachnifera* Torr.×*Poa pratensis* L. hybrid designated as 'HB 129' has been disclosed in pending U.S. patent application Ser. No. 11/197,945, filed Aug. 5, 2005, claiming the benefit of provisional application No. 60/599,539, filed Aug. 6, 2004. 'HB 129' is commercially available as 'Thermal Blue' and this commercial designation is used elsewhere herein.

U.S. Plant Pat. No. 18,439, filed Aug. 19, 2005, described another *Poa arachnifera* Torr.×*Poa pratensis* L. hybrid designated as 'HB 329' as the progeny formed by crossing an interspecific hybrid bluegrass (Texas Bluegrass×Kentucky Bluegrass) designated 'HB 47' (a female plant 7-23× cv. 'Geronimo' male plant ) as the female parent crossed with cv. 'Ascot' Kentucky bluegrass (Poa pratensis L.) as the pollen parent. 'HB 329' is commercially available as 'Dura Blue' and this commercial designation is used elsewhere herein.

U.S. patent application Ser. No. 11/483,919, filed Jul. 10, 2006, described another *Poa arachnifera* Torr.×*Poa pratensis* L. hybrid designated as 'HB 130'. 'HB 130' bluegrass is the progeny of Texas bluegrass (*Poa arachnifera* Torr.) female plant 6–8 (seed parent), with cv. 'Geronimo' Kentucky bluegrass (pollen parent) (*Poa pratensis* L.). 'HB 130' is commercially available as 'Solar Green' and this commercial designation is used elsewhere herein.

SUMMARY OF THE VARIETY

'HB 328' bluegrass originated as the progeny formed by crossing an interspecific hybrid bluegrass (*Poa arachnifera* Torr.×*Poa pratensis* L.) designated 'HB 13' (a female plant 6–17×cv. 'Geronimo' male plant) as the female parent crossed with cv. 'Ascot' Kentucky bluegrass (*Poa pratensis* L.) as the pollen parent. As a result of this breeding, a distinct hybrid variety was produced asexually propagated by rhizomes, tillers and disseminules displaying perfect flowers, apomixis and turfgrass performance characteristics in the $F_1$ generation.

Interspecific hybrid bluegrass female plant 'HB 13' is an unreleased plant selected and maintained in Gervais, Oreg., for its tiller density, turf quality and lack of male reproductive organs. 'Ascot' Kentucky bluegrass was bred at Marysville, Ohio, and has been disclosed under the designation 'BA 77-279' Kentucky Bluegrass in U.S. Plant Pat. No. 9,977 P, issued Jul. 22, 1997. 'HB 328' is distinguishable from its maternal parent 'HB 13' in view of the fact that 'HB 328' florets are perfect since they possess both stamens and pistils. To the contrary, 'HB13' florets are not perfect since they possess pistils, but no stamens. Furthermore, 'HB 328' can produce pollen whereas 'HB 13' cannot.

The highly apomictic seed of 'HB 328' bluegrass was produced first as Gervais, Oreg. This seed was used to plant turf performance evaluation trials and later, seed production fields. The seed of 'HB 328' has been found to be stable. Asexual production of 'HB 328' initially was performed at Gervais, Oreg. by propagules (tillers and rhizomes) and by disseminules (modified caryopses produced by apomixis), and has consistently produced progeny plants indistinguishable from the first generation asexual reproductions of the instant plant. The apomixis level of 'HB328' is approximately 88.5%. The apomixis level was determined by examining field planting of 'HB 328' in two years of rating for apomictic origin and from plants grown in a controlled environment chamber from disseminules harvested over four growing seasons from field grown plants in Gervais, Oreg.

'HB 328' has a number of highly desirable characteristics, including a dark green color, excellent cold tolerance, and good rust and dollarspot disease tolerance. 'HB 328' has an upright, semi-erect leafy turf type growth habit. The dark green color of 'HB 328' turf can be maintained throughout an entire growing season and 'HB 328' demonstrates excellent fall color and superior winter color under mild winter conditions. 'HB 328' has exhibited better rhizome growth relative to other varieties and tends to regrow faster during spring green-up.

'HB 328' has an amount of cotton (webbing) on the caryopsis, lemma and panicle, comparable to that found in 'HB 329'. Individual 'HB 328' seeds are larger than those of comparable varieties. In comparison with 'HB 129' and 'Reveille' hybrids, the number and percent of area covered by 'HB 328' seedlings is lower than 'HB 129' but greater than 'Reveille'. 98 days after sowing. Individual 'HB 328' seedlings were larger than either 'Reveille' or 'HB 129' seedlings.

In comparison with a number of Kentucky bluegrass varieties and with hybrid bluegrass varieties such as 'HB 129' and 'Reveille', unmoved mature plants of 'HB 328' are semi-erect and short, with shorter tiller culms and whole plants than 'HB 129' and 'Reveille'. 'HB 328' has medium to wide and short vegetative leaves.

Tillers of 'HB 328' are shorter than those of 'HB 129' but longer than 'Reveille', and have fewer nodes with shorter internode lengths than most other tested varieties, including 'HB 129' and 'Reveille'. Flag leaves of 'HB 328' are of intermediate length and width but are relatively thick with short sheaths and average hair density.

Panicles of 'HB 328' are open with a growth habit between nodding and upright. 'HB 328' panicles have slightly more whorls per panicle than 'HB 129' and 'Reveille' panicles.

DETAILED DESCRIPTION OF THE VARIETY

Figure 1:
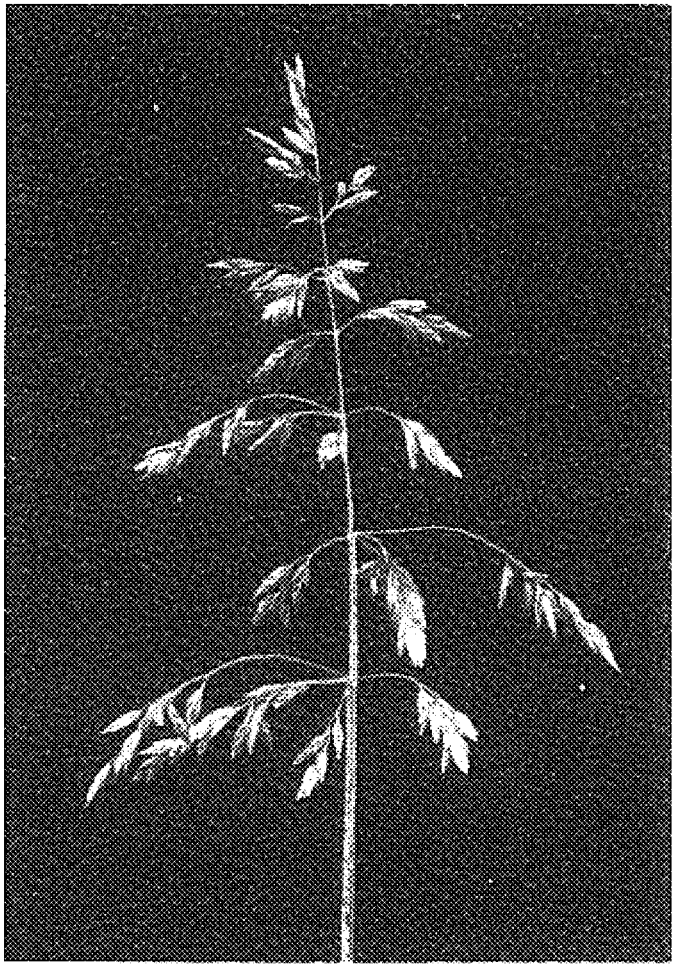
FIG. 1 is an 'HB 328' panicle.
Figure 2:
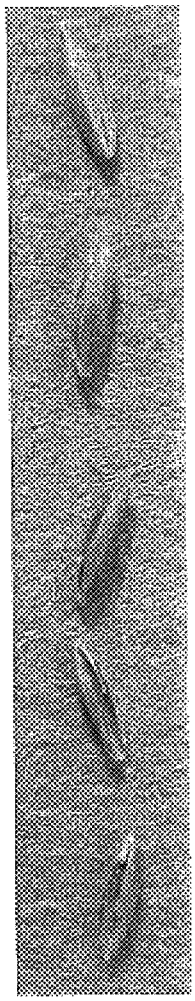
FIG. 2 is several 'HB 328' seeds.
Figure 3:
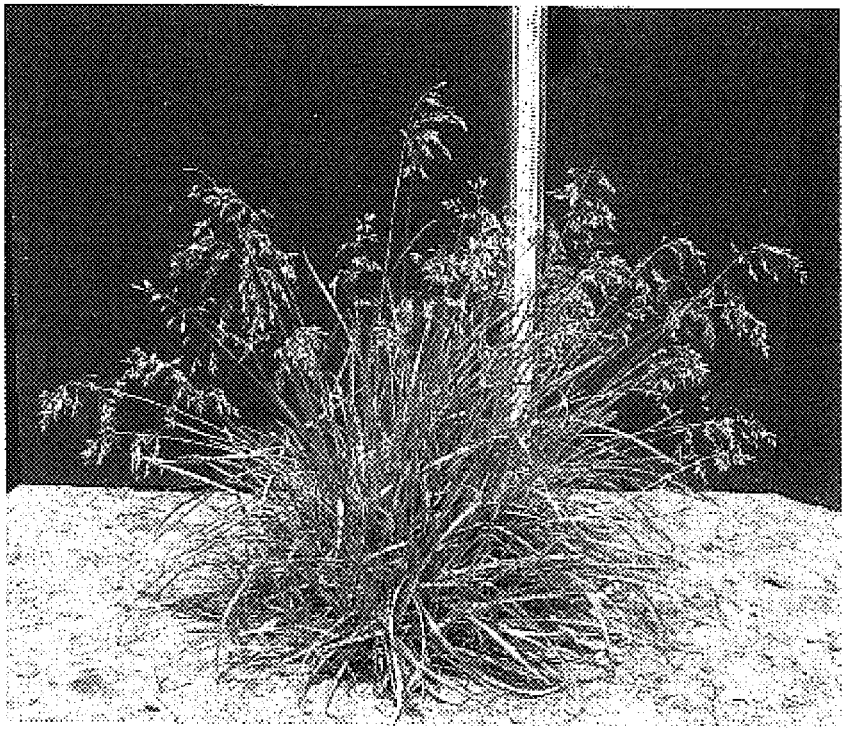
FIG. 3 is an 'HB 328' plant shortly after completing anthesis.

'HB 328' (*Texas bluegrass*×*Kentucky bluegrass*)×*Kentucky bluegrass hybrid which may also be designated as* (*Poa arachnifera Torr.*×*Poa pratensis* L.)×*Poa pratensis L.* hybrid is perennial with creeping rhizomes forming a moderately dense turf.

Hybrid bluegrass 'HB 328' is distinct from other varieties of bluegrass in morphological and growth characteristics. Since environmental conditions such as soil and climate may influence morphological characteristics to some extent, comparisons of 'HB 328' were made with Kentucky, Tex., and hybrid bluegrass varieties including 'HB 129' and 'Reveille' hybrid bluegrass under like conditions and the comparisons are set forth in Table 1–17, as follows.

TABLE 1

Comparison of Heading Dates and Anthesis Dates of various Kentucky and Texas bluegrass cultivars planted in the nurseries at Gervais, Oregon.

| | Heading Date | Anthesis Date | Heading Date | Anthesis Date |
|---|---|---|---|---|
| Growing Season | 2005 | 2005 | 2006 | 2006 |
| 'HB 328' | 118.4 | 135.6 | 135.4 | 143.5 |
| 'HB 129' | 119.5 | 138.0 | 133.4 | 138.4 |
| 'HB 130' | 121.5 | 140.8 | 133.1 | 140.8 |
| 'HB 329' | 123.0 | 144.8 | 135.6 | 142.7 |
| 'Ascot' | 123.7 | 140.5 | 135.8 | 141.1 |
| 'Geronimo' | 121.6 | 139.9 | 127.6 | 136.5 |
| 'TX 46 90' | | | 123.7 | |
| 'TX 51-90' | 116.2 | 139.7 | 127.1 | 137.7 |
| 'TX-39-88' | 121.4 | | | |
| 'TX 49-90' | 119.2 | 139.5 | | 139.0 |
| 'Reveille' | 115.8 | 141.4 | 130.8 | 146.4 |
| 'Kelly' | 130.8 | 143.4 | 138.7 | 145.5 |
| LSD (p = 0.05) | 5. | 4.85 | 6.54 | 3.58 |

Growth of 'HB 328' plants is characterized in part by tillering. Tiller culms of 'HB 328' are relatively short, have relatively few nodes and short internode length (See Table 2).

TABLE 2

Comparison of Tiller Characteristics of 'HB 328' and various Kentucky and Texas bluegrass cultivars planted in the nurseries at Gervais, Oregon. Measurements in this Table are in centimeters (cm) or by number (count).

| | Tiller Culm Length (cm) | Tiller Culm Length (cm) | Number of Nodes Per Tiller | Number Nodes Tiller | Top Internode Length (cm) | Top Intern Length (cm) |
|---|---|---|---|---|---|---|
| Growing Season | 2005 | 2005 | 2005 | 2005 | 2005 | 2005 |
| 'HB 328' | 56.7 | 55.7 | 3.0 | 3.4 | 8.1 | 9.9 |
| 'HB 129' | 59.2 | 64.8 | 4.5 | 4.7 | 11.3 | 13.5 |
| 'HB 130' | 58.5 | 63.0 | 4.4 | 3.9 | 11.5 | 13.1 |
| 'HB 329' | 52.6 | 52.3 | 3.2 | 4.2 | 17.0 | 17.8 |
| 'Abbey' | 56.7 | | | 4.1 | | 15.7 |
| 'Ascot' | 47.0 | 52.4 | 4.1 | 4.8 | 9.7 | 10.8 |
| 'Geronimo' | 59.3 | | 4.7 | 4.1 | 12.5 | 15.5 |
| 'TX 19-88' | 70.0 | | | 3.8 | | 9.5 |
| 'TX 46-90' | 61.7 | 66.5 | | 3.4 | | 9.8 |
| 'TX 4-88' | 79.5 | | | 4.1 | | 12.0 |
| 'TX 51-90' | | 51.9 | 2.3 | | 11.2 | |
| 'TX-39-88' | | 66.5 | 2.2 | | 9.9 | |
| 'TX 49-90' | | | 2.4 | | 9.7 | |
| 'Reveille' | | 62.6 | 2.8 | | 13.9 | |
| 'Kelly' | | 54.9 | 4.1 | | 9.6 | |
| LSD (p = 0.05) | 7.59 | 7.77 | 1.1 | 0.86 | 3.39 | 3.5 |

When plants overwinter in the field and grow undisturbed by clipping they reached 42.5 cm, 40.4 cm, and 36.7 cm in three different years. See Table 3. In each year their was shorter than 'HB 129' but slightly taller than hybrid 'HB 329'. 'HB 328' growth habit is semi-erect. See Table 4.

TABLE 3

Comparison of Plant Height of 'HB 328' and various Kentucky and Texas bluegrass cultivars planted in the nurseries at Gervais, Oregon. Measurements in this Table are in centimeters (cm).

| | Plant Height (cm) | Plant Height (cm) | Plant Height (cm) |
|---|---|---|---|
| Growing Season | 2004 | 2005 | 2006 |
| 'HB 328' | 42.5 | 40.4 | 36.7 |
| 'HB 129' | 63.5 | 58.3 | 57.2 |
| 'HB 130' | 66.5 | 54.6 | 54.9 |
| 'HB 329' | 34.0 | 35.8 | 37.9 |
| 'Abbey' | 64.6 | | |
| 'Ascot' | 36.7 | 38.2 | 32.0 |
| 'Geronimo' | 62.4 | 56.8 | 54.7 |
| 'TX 19-88' | 59.8 | | |
| 'TX 46-90' | 45.4 | 56.2 | 46.9 |
| 'TX 4-88' | 59.8 | | |
| 'TX 51-90' | | 48.1 | 49.6 |
| 'TX-39-88' | | 60.4 | |
| 'Reveille' | | | 54.9 |
| 'Kelly' | | 38.0 | 43.0 |
| LSD (p = 0.05) | 8.89 | 8.80 | 6.54 |

TABLE 4

Comparison of Growth Habit of 'HB 328' and various Kentucky and Texas bluegrass cultivars planted in the nurseries at Gervais, Oregon, after one and two years. (Ratings in this Table 4 were as follows: 1 = prostrate, 2 = semi-erect, 3 = erect).

| | Growth Habit | Growth Habit | Growth Habit |
|---|---|---|---|
| Growing Season | 2005 | 2004 | 2006 |
| 'HB 328' | 2.0 | 2.0 | 1.1 |
| 'HB 129' | 2.1 | 2.3 | 2.0 |
| 'HB 130' | 2.4 | 2.3 | 2.0 |
| 'HB 329' | 1.8 | 2.0 | 2.0 |
| 'Abbey' | | 2.4 | |
| 'Ascot' | 2.4 | 1.7 | 1.0 |
| 'Geronimo' | 1.9 | 2.3 | 1.7 |
| 'TX 19-88' | 3.0 | 3.0 | |
| 'TX 46-90' | 3.0 | 2.5 | |
| 'TX 4-88' | 3.0 | 1.5 | |
| 'Reveille' | | | 3.0 |
| 'Kelly' | | | 1.2 |
| LSD (p = 0.05) | 0.34 | 0.35 | 0.15 |

TABLE 5

Comparison of Vegetative Leaf Characteristics of 'HB 328' and various Kentucky and Texas bluegrass cultivars planted the nursery at Gervais, Oregon. Measurements in this Table are in centimeters (cm).

| | Vegetative Leaf Length | Vegetative Leaf Length | Vegetative Leaf Width |
|---|---|---|---|
| Growing Season | 2005 | 2005 | 2005 |
| 'HB 328' | 7.8 | 12.5 | .41 |
| 'HB 129' | 9.4 | 7.0 | .46 |
| 'HB 130' | 9.0 | 7.9 | .46 |
| 'HB 329' | 9.4 | 7.9 | .49 |
| 'Abbey' | | 7.8 | |
| 'Ascot' | 8.6 | 6.9 | .37 |
| 'Geronimo' | 9.1 | 8.0 | .46 |
| 'TX 19-88' | | 14.2 | |
| 'TX 46-90' | | 15.4 | |
| 'TX 4-88' | | 15.6 | |
| 'TX 51-90' | 9.1 | | .36 |
| 'TX-39-88' | 9.0 | | .46 |
| 'TX 49-90' | 12.3 | | .59 |
| 'Reveille' | 9.2 | | .29 |

TABLE 5-continued

Comparison of Vegetative Leaf Characteristics of 'HB 328' and various Kentucky and Texas bluegrass cultivars planted the nursery at Gervais, Oregon. Measurements in this Table are in centimeters (cm).

| | Vegetative Leaf Length | Vegetative Leaf Length | Vegetative Leaf Width |
|---|---|---|---|
| 'Kelly' | 9.1 | | .39 |
| LSD (p = 0.05) | 3.29 | 3.35 | .101 |

When grass growth changes from vegetative to reproductive, grass flower heads are surrounded by the flag leaf. As the flowers mature and emerge, the flag leaf remains attached near the base of the flower head. The 'HB 328' flag leaf sheath type is closed and the 'HB 328' flag leaf sheath, at 13.1 cm, and the flag leaf, at 6.8 cm, are both shorter than those of 'HB 129' and 'Reveille' plants. The 'HB 328' flat leaf, at 0.37 cm, is narrower than that of 'HB 129' but wider than that of 'Reveille' plants (see Table 6). The flag leaf averages fewer hairs on the ligule than 'HB 129' hybrid blue grass but more than on the 'Reveille' ligule (See Table 7).

TABLE 6

Comparison of Flag Leaf Characteristics of 'HB 328' and various Kentucky and Texas bluegrass cultivars planted in the nurseries at Gervais, Oregon. Measurements in this Table are in centimeters (cm).

| | Flag Leaf Sheath Length | Flag Leaf Length | Flag Leaf Width |
|---|---|---|---|
| Growing Season | 2005 | 2005 | 2005 |
| 'HB 328' | 13.1 | 6.8 | .37 |
| 'HB 129' | 15.5 | 7.2 | .40 |
| 'HB 130' | 15.3 | 6.5 | .40 |
| 'HB 329' | 13.7 | 6.4 | .38 |
| 'Ascot' | 13.2 | 5.7 | .32 |
| 'Geronimo' | 15.3 | 6.7 | .42 |
| 'TX 51-90' | 12.3 | 8.0 | .41 |
| 'TX-39-88' | 15.8 | 8.7 | .49 |
| 'TX 49-90' | 15.6 | 9.7 | .56 |
| 'Reveille' | 16.4 | 7.6 | .32 |
| 'Kelly' | 14.4 | 6.1 | .36 |
| LSD (p = 0.05) | 2.78 | 2.72 | .121 |

TABLE 7

Comparison of Ligule Thickness, Ligule Hairs and Flag Leaf Thickness of 'HB 328' and various Kentucky and Texas bluegrass cultivars in the nurseries at Gervais, Oregon.

| | Flag Leaf Ligule Length (mm) | Flag Leaf Ligule Hairs 9 = Many 1 = none | Flag Leaf Thickness (mm) |
|---|---|---|---|
| Growing Season | 2005 | 2005 | 2005 |
| 'HB 328' | 2.43 | 5.1 | 0.0202 |
| 'HB 129' | 1.33 | 5.8 | 0.0149 |
| 'HB 130' | 1.66 | 4.5 | 0.0145 |
| 'HB 329' | 2.25 | 3.2 | 0.0182 |
| 'Ascot' | 2.00 | 5.6 | 0.0166 |
| 'Geronimo' | 1.67 | 7.1 | 0.0164 |
| 'TX 51-90' | 1.68 | 0.1 | 0.0262 |
| 'TX-39-88' | 2.65 | 0.1 | 0.0199 |
| 'TX 49-90' | 2.00 | 0.5 | 0.0231 |
| 'Reveille' | 2.32 | 0.9 | 0.0207 |
| 'Kelly' | 2.05 | 6.3 | 0.0163 |
| LSD (p = 0.05) | 0.663 | 1.93 | 0.00332 |

Bluegrass flower heads (inflorescences) have a panicle morphology. See FIG. 1. 'HB 328' panicles have a semi-nodding habit, averaging 10.6 and 10.7 cm in length and 9.7 and 8.0 cm in width in two nursery plantings, respectively. This is similar to 'HB 129' and 'Reveille'. 'HB 328' panicles average 8.8 and 8.9 whorls per panicle in two nursery plantings, respectively, more than either 'HB 129' or 'Reveille' (See Table 8). 'HB 328' panicles on average have 4.8 branches on the lowest whorl ($1^{st}$ whorl) and 3.5 branches on the $3^{rd}$ whorl, more than 'HB 129' (see Table 9). 'HB 328' has 5.2 florets per spikelet on the $1^{st}$ whorl and 5.0 florets per spikelet on the $3^{rd}$ whorl. The glumes of the first whorl are 3.4 mm in length and 3.8 mm in width, while glumes of the third whorl are 3.6 mm in length and 3.9 mm in width (See Table 10).

TABLE 8

Comparison of Panicle Characteristics of 'HB 328' and various Kentucky and Texas bluegrass cultivars planted in the nurseries at Gervais, Oregon. Measurements of Panicle Length and Width in this Table are in centimeters (cm).

| | Panicle Habit | Panicle Habit | Panicle Length (cm) | Panicle Length (cm) | Panicle Width (cm) | Panicle Width (cm) |
|---|---|---|---|---|---|---|
| Growing Season | 2004 | 2006 | 2005 | 2005 | 2005 | 2005 |
| 'HB 328' | 1.5 | 1.2 | 10.7 | 10.6 | 9.7 | 8.0 |
| 'HB 129' | 2.0 | 1.1 | 10.5 | 9.1 | 10.3 | 8.4 |
| 'HB 130' | 2.0 | 1.1 | 10.7 | 9.3 | 10.8 | 8.5 |
| 'HB 329' | 1.8 | 1.4 | 9.7 | 8.6 | 8.5 | 6.7 |
| 'Abbey' | 1.3 | | | 12.5 | | 6.9 |
| 'Ascot' | 1.2 | | 8.9 | 7.6 | 7.2 | 7.0 |
| 'Geronimo' | 2.0 | 1.1 | 11.1 | 8.9 | 11.4 | 8.9 |
| 'TX 19-88' | 1.8 | | | 12.8 | | 9.8 |
| 'TX 46-90' | 1.8 | | | 13.5 | | 9.5 |
| 'TX 4-88' | 1.8 | | | 13.7 | | 9.2 |
| 'TX 51-90' | | 1.3 | 10.6 | | 9.3 | |
| 'TX-39-88' | | 1.9 | 11.5 | | 9.1 | |
| 'TX 49-90' | | 1.2 | 9.6 | | 7.4 | |
| 'Reveille' | | 1.9 | 10.9 | | 9.1 | |
| 'Kelly' | | 1.5 | 9.8 | | 9.4 | |
| LSD (p = 0.05) | 0.28 | | 2.51 | 2.65 | 1.91 | 1.24 |

| | Number of Whorls in Panicle | Number of Whorls in Panicle | Panicle Branch Attitude | Panicle Branch Attitude | Panicle Branch Attitude |
|---|---|---|---|---|---|
| Growing Season | 2005 | 2005 | 2006 | 2005 | 2004 |
| 'HB 328' | 8.9 | 8.8 | 2.0 | 1.3 | 1.0 |
| 'HB 129' | 8.6 | 8.0 | 1.9 | 1.0 | 1.1 |
| 'HB 130' | 8.9 | 8.2 | 2.0 | 1.0 | 1.0 |
| 'HB 329' | 8.1 | 8.3 | 2.0 | 1.5 | 1.1 |
| 'Abbey' | 9.3 | | | 1.0 | 1.1 |
| 'Ascot' | 7.0 | 7.2 | 1.9 | 1.2 | 1.5 |
| 'Geronimo' | 8.9 | 8.4 | 1.8 | 1.3 | 1.2 |
| 'TX 19-88' | | | | 3.0 | 3.0 |
| 'TX 46-90' | 9.9 | | | 2.9 | 2.5 |
| 'TX 4-88' | 10.0 | | | 2.8 | 1.5 |
| 'TX 51-90' | | 7.2 | 2.7 | | |
| 'TX-39-88' | | 7.2 | 2.9 | | |
| 'TX 49-90' | | 7.9 | | | |
| 'Reveille' | | 7.6 | 3.0 | | |
| 'Kelly' | | 8.2 | 2.3 | | |
| LSD (p = 0.05) | 0.53 | 1.37 | 0.39 | 0.54 | |

Panicle Habit:
1 = Nodding
2 = Upright
Panicle Branch Attitude:
1 = Drooping
2 = Horizontal
3 = Ascending

TABLE 9

Comparison of Panicle Characteristics of 'HB 328' and various Kentucky and Texas bluegrass cultivars planted in the nurseries at Gervais, Oregon.

| | Number of Branches in Lowest Whorl of Panicle | Number of Branches in 3rd Whorl of Panicle | Panicle type 1 = Open 2 = Intermediate 3 = Compact |
|---|---|---|---|
| Growing Season | 2005 | 2005 | 2004 |
| 'HB 328' | 4.8 | 3.5 | 1.0 |
| 'HB 129' | 4.0 | 3.3 | 1.0 |
| 'HB 130' | 3.9 | 3.2 | 1.0 |
| 'HB 329' | 4.4 | 3.8 | 1.0 |
| 'Abbey' | 3.1 | 3.1 | 1.0 |
| 'Ascot' | 2.8 | 2.4 | 1.0 |
| 'Geronimo' | 4.0 | 3.5 | 1.0 |
| 'TX 19-88' | 5.3 | | 2.0 |
| 'TX 46-90' | 4.9 | 5.0 | 2.0 |
| 'TX 4-88' | 5.7 | 6.5 | 2.0 |
| 'TX 51-90' | | | |
| 'TX-39-88' | | | |
| 'TX 49-90' | | | |
| 'Reveille' | | | |
| 'Kelly' | | | |
| LSD (p = 0.05) | 0.81 | 0.75 | 0.00 |

| | Panicle type 1 = Open 2 = Intermediate 3 = Compact | Panicle Type % Open | Panicle Type % Intermediate | Panicle type % Compact |
|---|---|---|---|---|
| Growing Season | 2006 | 2005 | 2005 | 2005 |
| 'HB 328' | 1.1 | 98.3 | 1.7 | 0 |
| 'HB 129' | 1.0 | 96.8 | 3.2 | 0 |
| 'HB 130' | 1.0 | 100.0 | 0 | 0 |
| 'HB 329' | 1.1 | 92.6 | 7.4 | 0 |
| 'Abbey' | | | | |
| 'Ascot' | 1.0 | 98.3 | 1.7 | 0 |
| 'Geronimo' | 1.0 | 100.0 | 0 | 0 |
| 'TX 19-88' | | | | |
| 'TX 46-90' | | | | |
| 'TX 4-88' | | | | |
| 'TX 51-90' | 2.7 | 0 | 25.0 | 75.0 |
| 'TX-39-88' | 2.9 | 0 | 15.4 | 84.7 |
| 'TX 49-90' | | 0 | 25.7 | 74.3 |
| 'Reveille' | 2.8 | 27.0 | 59.8 | 13.2 |
| 'Kelly' | 1.0 | | 98.4 | 0 |
| LSD (p = 0.05) | 0.190 | 12.79 | 15.36 | 10.13 |

TABLE 10

Comparison of Panicle Characteristics of 'HB 328' and various Kentucky and Texas bluegrass cultivars harvested from a field nursery at Gervais, Oregon. Measurements in this Table are in millimeters (mm).

| | Spikelet Length $1^{st}$ Whorl (mm) | Spikelet Width $1^{st}$ Whorl (mm) | Spikelet Length $3^{rd}$ Whorl (mm) | Spikelet Width $3^{rd}$ Whorl (mm) | Glume #1 Length $1^{st}$ Whorl (mm) | Glume #2 Width $1^{st}$ Whorl (mm) |
|---|---|---|---|---|---|---|
| Growing Season | 2005 | 2005 | 2005 | 2005 | 2005 | 2005 |
| 'HB 328' | 6.6 | 5.2 | 6.8 | 4.4 | 3.4 | 3.8 |
| 'HB 129' | 7.6 | 4.5 | 7.1 | 4.0 | 3.1 | 3.5 |
| 'HB 130' | 6.4 | 4.2 | 6.7 | 3.6 | 3.0 | 3.0 |
| 'HB 329' | 6.2 | 4.3 | 6.5 | 3.8 | 3.7 | 3.6 |
| 'Ascot' | 5.6 | 4.4 | 5.8 | 4.3 | 2.9 | 3.1 |
| 'Geronimo' | 5.5 | 4.2 | 6.3 | 4.0 | 2.7 | 2.9 |
| 'TX 51-90' | 7.6 | 7.3 | 7.5 | 7.1 | 3.6 | 4.2 |
| 'TX-39-88' | 8.6 | 5.9 | 8.5 | 5.7 | 3.6 | 4.0 |

TABLE 10-continued

Comparison of Panicle Characteristics of 'HB 328' and various Kentucky and Texas bluegrass cultivars harvested from a field nursery at Gervais, Oregon. Measurements in this Table are in millimeters (mm).

| | | | | | | |
|---|---|---|---|---|---|---|
| 'TX 49-90' | 9.7 | 8.2 | 9.7 | 8.0 | 5.4 | 6.0 |
| 'Reveille' | 6.1 | 4.0 | 6.4 | 4.2 | 2.9 | 3.3 |
| 'Kelly' | 6.3 | 4.4 | 6.1 | 4.3 | 2.8 | 3.0 |
| LSD (p = 0.05) | 1.68 | 1.88 | 1.74 | 1.62 | 0.85 | 0.95 |

| | Glume #1 Length 3rd Whorl (mm) | Glume #2 Length 3rd Whorl (mm) | Number of Florets Per Spikelet in 1st Whorl | Number of Florets Per Spikelet in 3rd Whorl |
|---|---|---|---|---|
| Growing Season | 2005 | 2005 | 2005 | 2005 |
| 'HB 328' | 3.6 | 3.9 | 5.2 | 5.0 |
| 'HB 129' | 3.2 | 3.3 | 8.6 | 7.0 |
| 'HB 130' | 3.0 | 3.2 | 6.3 | 6.4 |
| 'HB 329' | 3.6 | 3.7 | 4.6 | 5.0 |
| 'Ascot' | 2.9 | 3.1 | 3.8 | 4.3 |
| 'Geronimo' | 3.0 | 3.1 | 5.2 | 6.0 |
| 'TX 51-90' | 3.3 | 4.2 | 8.8 | 8.5 |
| 'TX-39-88' | 3.6 | 4.2 | 8.0 | 7.9 |
| 'TX 49-90' | 5.0 | 5.4 | 8.7 | 8.6 |
| 'Reveille' | 3.3 | 3.5 | 4.0 | 4.9 |
| 'Kelly' | 2.9 | 3.0 | 4.3 | 4.9 |
| LSD (p = 0.05) | 0.68 | 0.80 | 1.69 | 1.81 |

The seed of 'HB 328' was conditioned by removing most of the extraneous materials that may have been harvested with the seed, such as small pieces of plant stems and leaves, soil particles, seed of other plants and the like. 'HB 328' seeds had a combined length of 37.7 mm and combined width of 9.4 mm, greater than all other tested varieties. Similarly, 'HB 328' seed was heavier than all other varieties (See Table 11). Seed and panicles of 'HB 328' were overall more heavily covered with cotton and webbing than either 'HB 129' or 'Reveille' but less than 'HB 329' (See Table 12).

TABLE 11

Comparison of seed size of 'HB 328' and various Kentucky and Texas bluegrass cultivars planted in a field nursery at Gervais, Oregon.

| | Length of 10 Seeds (mm) | Width of 10 Seeds (mm) | Weight of 1000 Seed Count (mg) |
|---|---|---|---|
| Growing Season | 2004 | 2004 | 2004 |
| 'HB 328' | 37.7 | 9.4 | 710.0 |
| 'HB 129' | 32.0 | 8.0 | 540.0 |
| 'HB 130' | 34.0 | 8.3 | 546.7 |
| 'HB 329' | 26.2 | 9.1 | 660.0 |
| 'Abbey' | 34.7 | 7.8 | 576.7 |
| 'Ascot' | 32.3 | 8.0 | 543.3 |
| 'Geronimo' | 30.3 | 8.1 | 516.7 |
| 'Unique' | 23.3 | 6.5 | 360.0 |
| LSD (p = 0.05) | 10.88 | 0.81 | 46.77 |

TABLE 12

Comparison of Seed properties of 'HB 328' and various Kentucky and Texas bluegrass cultivars planted in the nurseries at Gervais, Oregon.

| | Lemma Cotton Density (Visual Rating) 5 = Most 1 = None | Lemma Cotton Density (Visual Rating) 5 = Most 1 = None | Panicle Cotton Density (Visual Rating) 5 = Most 1 = None | Lemma Length (mm) | Lemma Length (mm) |
|---|---|---|---|---|---|
| Growing Season | 2005 | 2005 | 2005 | 2005 | 2005 |
| 'HB 328' | 3.0 | 3.4 | 3.8 | 4.6 | 4.4 |
| 'HB 129' | 2.2 | 3.3 | 2.0 | 3.8 | 3.8 |
| 'HB 130' | 2.2 | 2.7 | 2.3 | 3.8 | 3.6 |
| 'HB 329' | 3.8 | 3.5 | 3.6 | 4.8 | 4.0 |
| 'Ascot' | 2.3 | 2.6 | 2.4 | 3.7 | 4.0 |
| 'Geronimo' | 2.3 | 2.6 | 2.1 | 3.8 | 3.6 |
| 'TX 51-90' | 3.5 | | 2.3 | 5.8 | |
| 'TX-39-88' | 3.7 | 2.4 | 3.8 | 6.2 | 4.9 |
| 'TX 49-90' | 3.7 | | 4.3 | 6.2 | |
| 'Reveille' | 3.0 | 3.5 | 2.3 | 4.2 | 3.8 |
| 'Kelly' | 2.3 | 2.6 | 2.7 | 3.8 | 4.9 |
| LSD (p = 0.05) | 0.29 | 1.39 | 0.74 | 0.47 | 0.79 |

| | Webbing Length % Of Lemma (%) | Webbing Length % Of Lemma (%) | Webbing Length (mm) |
|---|---|---|---|
| Growing Season | 2005 | 2005 | 2005 |
| 'HB 328' | 93.3 | 100.8 | 3.0 |
| 'HB 129' | 80.0 | 84.2 | 2.2 |
| 'HB 130' | 74.6 | 76.9 | 2.2 |
| 'HB 329' | 108.3 | 47.7 | 3.8 |
| 'Ascot' | 61.3 | 75.6 | 2.4 |
| 'Geronimo' | 89.6 | 59.4 | 2.3 |
| 'TX 51-90' | 132.3 | | 3.5 |
| 'TX-39-88' | 132.1 | 70.3 | 3.7 |
| 'TX 49-90' | 120.8 | | 3.7 |
| 'Reveille' | 95.4 | 84.7 | 3.0 |
| 'Kelly' | 88.3 | 65.8 | |
| LSD (p = 0.05) | 26.3 | 46.4 | 0.29 |

Seedlings of 'HB 328' are individually heavier than seedlings of other tested bluegrasses, while the absolute number of seedlings per area and the rate of ground coverage by 'HB 328' is better than 'Reveille' and not as fast as 'HB129'. See Table 14. After five months of growth, 'HB 328' plants had more rhizomes, 12.5, than other compared bluegrasses. Plant spread following five months of growth, 230 $cm^2$, was greater than spread of 'HB 129' and 'HB 329' hybrids but less than the spread of 'HB 130' hybrid bluegrass. See Table 16.

Turf of 'HB 328' has a dark green color that can be maintained throughout the growing season. The upper and lower leaf blade surface colors of 'HB 328' were determined by comparing several actively growing leaves on at a time, in full sun, with color chips from the Munsell Book of Color as a reference. On this basis, the color of the upper and lower leaf blade surfaces were determined by comparable ranging from 7.5 GY 4/6 to 2.5 G 4/6. Additionally, color designations were determined from tillers harvested from the plant nursery using the Munsell Book of Color, Volume 1 of a two volume set, as follows: 10 YR 6/4 for 'HB 328' seed; 10 YR 7/4 for the 'HB 328' spikelet; and 10 YR 7/6 for the 'HB 328' culm. 'HB 328' shows better fall and winter color compared with the other Kentucky bluegrass varieties and hybrids tested, including 'HB 129', 'HB 130', and 'Reveille' bluegrasses (see Table 13). Over two thirds of 'HB 328' turf remained green during the winter, and almost no cold stress was observed, better than other tested bluegrasses including 'HB 129' and 'Reveille' (See Table 15). It should be noted that the general apparent color of turf does not always correlate with the color of the individual actively growing leaves within the turf and that turf color as well as leaf, seed, spikelet and culm colors may vary with nutrient levels, time of the year harvested, climatic conditions and such factors.

TABLE 13

Comparison of Turf Color of 'HB 328' and various Kentucky and Texas bluegrass cultivars grown as turf throughout the growing season in Gervais, Oregon and Valley Center, California.

| | Turf Color (March) Oregon 9 = Dark Green | Turf Color (June) Oregon 9 = Dark Green | Turf Color (June) California 9 = Dark Green | Turf Color (September) California 9 = Dark Green | Turf Color (January) California 9 = Dark Green |
|---|---|---|---|---|---|
| Growing Season | 2004 | 2004 | 2003 | 2003 | 2004 |
| 'HB 328' | 7.0 | 8.0 | 7.7 | 6.0 | 7.0 |
| 'HB 129' | 7.0 | 5.0 | 6.0 | 5.0 | 4.3 |
| 'HB 130' | 6.0 | 6.0 | 5.7 | 5.7 | 4.3 |
| 'HB 329' | 6.7 | 8.0 | 8.0 | 6.2 | 5.7 |
| 'Abbey' | 6.7 | 6.0 | 6.0 | 5.7 | 5.3 |
| 'Ascot' | 6.0 | 7.0 | | | |
| 'Geronimo' | 6.0 | 5.0 | | | |
| 'Reveille' | 3.3 | 7.0 | | | |
| 'Kelly' | 6.0 | 6.0 | | | |
| 'Apollo' | | | 7.3 | 6.5 | 5.0 |
| 'Midnight' | | | 7.3 | 7.8 | 6.0 |
| LSD (p = 0.05) | 1.58 | 0.41 | 0.68 | 0.76 | 1.25 |

TABLE 14

Comparison of Seedling Growth of 'HB 328' and various Kentucky and Texas bluegrass cultivars grown as turf at Gervais, Oregon.

| | Seedling Coverage (11 Days) Fall Plant (%) | Seedling Coverage (21 Days) Fall Plant (%) | Seedling Coverage (42 Days) Fall Plant (%) | Seedlings per sq ft (98 Days) Fall Plant Count | Dry Weight per Seedling (98 Days) Fall Plant Gram |
|---|---|---|---|---|---|
| Growing Season | 2004 | 2004 | 2004 | 2004 | 2004 |
| 'HB 328' | 30.0 | 56.7 | 73.3 | 590 | 0.0277 |
| 'HB 129' | 51.7 | 76.3 | 91.7 | 1720 | 0.0177 |
| 'HB 130' | 31.7 | 68.3 | 83.3 | 717 | 0.0350 |
| 'HB 329' | 21.7 | 56.7 | 70.0 | 676 | 0.0207 |
| 'Abbey' | 46.7 | 75.0 | 91.7 | 917 | 0.0240 |
| 'Ascot' | 46.7 | 71.7 | 85.0 | 1097 | 0.0261 |
| 'Geronimo' | 35.0 | 73.3 | 85.0 | 1187 | 0.0210 |
| 'Reveille' | 1.0 | 10.0 | 28.3 | 347 | 0.0091 |
| 'Kelly' | 53.3 | 81.7 | 90.0 | 1145 | 0.0257 |
| LSD (p = 0.05) | 7.35 | 6.95 | 6.36 | 475 | 0.00709 |

TABLE 15

Comparison of Cold Tolerance of 'HB 328' and various Kentucky and Texas bluegrass cultivars grown as turf in California and Oregon and in nursery plantings in Oregon

| | Winter Green (%) | Winter Green (%) | Cold Stress 0 = None (%) | Winter Plant Area ($cm^2$) |
|---|---|---|---|---|
| Month | January | February | January | January |
| Growing Season | 2005 | 2003 | 2005 | 2006 |
| 'HB 328' | 66.7 | 77.5 | 3.0 | 1520 |
| 'HB 129' | 20.0 | 35.0 | 33.3 | 2280 |
| 'HB 130' | 18.3 | 30.0 | 20.0 | 2376 |
| 'HB 329' | 56.7 | 52.5 | 10.0 | 1096 |
| 'Abbey' | | 30.0 | 43.3 | |
| 'Envicta' | 21.7 | | | |
| 'Avalanche' | 46.7 | | 2.0 | |
| 'Geronimo' | | | 33.3 | 2178 |
| 'Ascot' | | | 38.3 | 950 |
| 'TX 51-90' | | | | 672 |
| 'TX-39-88' | | | | 385 |
| 'TX 49-90' | | | | 337 |
| 'Reveille' | | | 2.7 | 1210 |
| 'Kelly' | | | 48.3 | 982 |
| LSD (p = 0.05) | 8.84 | 11.19 | 14.8 | 653 |

TABLE 16

Comparison of Rhizome Development (Count) and Plant Spread (Area) of Individual Seedling and Spring Surge Growth as Turf of 'HB 328' and various Kentucky and Texas bluegrass cultivars in Oregon.

| | Rhizomes per Plant @ 5 Months Oregon (Count) | Plant Spread July @ 5- Months Oregon ($cm^2$) | Turf Surge Growth Spring (March) Oregon Height (cm) |
|---|---|---|---|
| Growing Season | 2006 | 2006 | 2005 |
| 'HB 328' | 12.5 | 230 | 6.7 |
| 'HB 129' | 10.2 | 190 | 9.0 |
| 'HB 130' | 12.2 | 287 | 8.3 |
| 'HB 329' | 6.7 | 125 | 5.0 |
| 'Ascot' | 5.5 | 153 | 5.1 |
| 'Abbey' | | | 6.2 |
| 'Geronimo' | 10.8 | 272 | 8.9 |
| 'Texas 632500' | 2.7 | 40 | |
| LSD (p = 0.05) | 4.75 | 133.2 | 1.8 |

'HB 328' hybrid bluegrass is moderately resistant to brown blight and very resistant to dollarspot and rust fungal diseases (See Table 17).

TABLE 17

Disease Resistance of 'HB 328' and various Kentucky and Texas bluegrass cultivars Grown as Turf Plantings at Gervais, Oregon and Valley Center, California.

| | Brown Blight December (Oregon) (%) | Rust June (Oregon) (%) | Rust March (California) (%) | Dollarspot September (California) (%) |
|---|---|---|---|---|
| Growing Season | 2005 | 2005 | 2003 | 2003 |
| 'HB 328' | 10.7 | 0.0 | 2.0 | 0.0 |
| 'HB 129' | 11.0 | 8.3 | 16.7 | 21.7 |
| 'HB 130' | 6.7 | 8.3 | 13.3 | 16.7 |
| 'HB 329' | 9.0 | 2.3 | 2.0 | 0.3 |
| 'Abbey' | 22.3 | 28.3 | 13.3 | 16.7 |
| 'Ascot' | 5.3 | 23.3 | | |
| 'Geronimo' | 11.7 | 15.0 | | |
| 'Reveille' | 0.0 | 1.3 | | |

TABLE 17-continued

Disease Resistance of 'HB 328' and various Kentucky and Texas bluegrass cultivars Grown as Turf Plantings at Gervais, Oregon and Valley Center, California.

| | Brown Blight December (Oregon) (%) | Rust June (Oregon) (%) | Rust March (California) (%) | Dollarspot September (California) (%) |
|---|---|---|---|---|
| 'Kelly' | 30.0 | 20.0 | | |
| 'Apollo' | | | 23.3 | 0.0 |
| 'Midnight' | | | 26.7 | 0.3 |
| LSD (p = 0.05) | 14.02 | | 10.27 | 10.56 |

What is claimed is:

1. A new and distinct hybrid variety of (Texas bluegrass× Kentucky bluegrass)×Kentucky bluegrass plant, as herein illustrated and described and characterized by a moderately rapid establishment; dark green color; short plant height; semi-erect growth habit; short tiller culms; a moderately wide leaf blade; large seed; short flag leaf; moderately aggressive rhizome growth; high cold resistance; and high resistance to rust and dollarspot diseases.

* * * * *